(12) United States Patent
Breslau et al.

(10) Patent No.: US 8,751,253 B2
(45) Date of Patent: Jun. 10, 2014

(54) BIOMEDICAL FEEDBACK METHOD AND SYSTEM

(75) Inventors: Franklin Charles Breslau, Teaneck, NJ (US); Robert J. Torres, Colleyville, TX (US)

(73) Assignee: International Business Machines Corporation, Armonk, NY (US)

(*) Notice: Subject to any disclaimer, the term of this patent is extended or adjusted under 35 U.S.C. 154(b) by 1593 days.

(21) Appl. No.: 11/874,258

(22) Filed: Oct. 18, 2007

(65) Prior Publication Data
US 2009/0106049 A1    Apr. 23, 2009

(51) Int. Cl.
*G06Q 50/00* (2012.01)
*G06Q 10/00* (2012.01)

(52) U.S. Cl.
USPC .................................................. 705/2; 705/3

(58) Field of Classification Search
USPC ............................................................. 705/2
See application file for complete search history.

(56) References Cited

U.S. PATENT DOCUMENTS 5,832,448 A * 11/1998 Brown ............................ 705/2
2004/0102931 A1 * 5/2004 Ellis et al. ..................... 702/188

OTHER PUBLICATIONS

Minetti, A feedback-controlled treadmill (treadmill-on-demand) and the spontaneous speed of walking and running in humans, Apr. 11, 2003, J Appl Physiol 95: 838-843.*

* cited by examiner

*Primary Examiner* — Tran Nguyen
(74) *Attorney, Agent, or Firm* — Schmeiser, Olsen & Watts; Lisa J. Ulrich

(57) ABSTRACT

A feedback method and system. The method includes a computing system identifying a user. A biomedical feedback software application is enabled for the user. The biomedical feedback software application in the computing system monitors a first group of current biomedical characteristics of the user. The feedback software application analyzes the first group of current biomedical characteristics of the user with respect to a profile associated with the user. An analysis report is generated in response to the analysis. The analysis report is presented to the user. The computing system monitors a response to the analysis report from the user.

20 Claims, 4 Drawing Sheets

BIOMEDICAL FEEDBACK METHOD AND SYSTEM

FIELD OF THE INVENTION

The present invention relates to a method and associated system for monitoring current biomedical characteristics of a user and providing feedback associated with the current biomedical characteristics.

BACKGROUND OF THE INVENTION

Monitoring user characteristics for a user and providing recommendations with respect to the user typically comprises an inefficient process with little flexibility. A user wishing to obtain recommendations for optimizing the attributes for the characteristics may have to be examined by a professional. An examination by a professional may be very costly and time consuming. Accordingly, there exists a need in the art to overcome at least some of the deficiencies and limitations described herein above.

SUMMARY OF THE INVENTION

The present invention provides a feedback method comprising:

identifying, by a computing system, a first user, wherein said computing system comprises a memory system, wherein said memory system comprises a first plurality of profiles and a biomedical feedback software application, and wherein said first plurality of profiles comprises first previously received data associated with various biomedical characteristics of said first user;

enabling, by said computing system, said biomedical feedback software application for said first user;

retrieving, by said computing system from said memory system, a first profile of said first plurality of profiles, said first profile associated with said first user and a first group of current biomedical characteristics of said first user;

monitoring, by said biomedical feedback software application, said first group of current biomedical characteristics;

analyzing, by said biomedical feedback software application, said first group of biomedical characteristics with respect to said first profile of said first plurality of profiles;

generating in response to said analyzing said first group of biomedical characteristics with respect to said first profile of said first plurality of profiles, by said biomedical feedback software application, a first analysis report comprising results of said analyzing said first group of biomedical characteristics with respect to said first profile of said first plurality of profiles; and presenting, by said computing system to said first user, said first analysis report monitoring, by said computing system, a response to said first analysis report from said first user.

The present invention provides a computing system comprising a processor coupled to a computer-readable memory unit, said memory unit comprising a first plurality of profiles, a biomedical feedback software application, and instructions that when executed by the processor implement a feedback method, wherein said first plurality of profiles comprises first previously received data associated with various biomedical characteristics of a first user, said method comprising:

identifying, by said computing system, said first user;

enabling, by said computing system, said biomedical feedback software application for said first user;

retrieving, by said computing system from said computer-readable memory unit, a first profile of said first plurality of profiles, said first profile associated with said first user and a first group of current biomedical characteristics of said first user;

monitoring, by said biomedical feedback software application, said first group of current biomedical characteristics;

analyzing, by said biomedical feedback software application, said first group of biomedical characteristics with respect to said first profile of said first plurality of profiles;

generating in response to said analyzing said first group of biomedical characteristics with respect to said first profile of said first plurality of profiles, by said biomedical feedback software application, a first analysis report comprising results of said analyzing said first group of biomedical characteristics with respect to said first profile of said first plurality of profiles; and presenting, by said computing system to said first user, said first analysis report monitoring, by said computing system, a response to said first analysis report from said first user.

The present invention provides a computer program product, comprising a computer readable medium comprising a computer readable program code embodied therein, said computer readable program code adapted to implement a feedback method within a computing system, said method comprising:

identifying, by said computing system, a first user, wherein said computer readable medium comprises a first plurality of profiles and a biomedical feedback software application, and wherein said first plurality of profiles comprises first previously received data associated with various biomedical characteristics of said first user;

enabling, by said computing system, said biomedical feedback software application for said first user;

retrieving, by said computing system from said computer readable medium, a first profile of said first plurality of profiles, said first profile associated with said first user and a first group of current biomedical characteristics of said first user;

monitoring, by said biomedical feedback software application, said first group of current biomedical characteristics;

analyzing, by said biomedical feedback software application, said first group of biomedical characteristics with respect to said first profile of said first plurality of profiles;

generating in response to said analyzing said first group of biomedical characteristics with respect to said first profile of said first plurality of profiles, by said biomedical feedback software application, a first analysis report comprising results of said analyzing said first group of biomedical characteristics with respect to said first profile of said first plurality of profiles; and presenting, by said computing system to said first user, said first analysis report monitoring, by said computing system, a response to said first analysis report from said first user.

The present invention provides a process for supporting computer infrastructure, said process comprising providing at least one support service for at least one of creating, integrating, hosting, maintaining, and deploying computer-readable code in a computing system comprising a memory unit, wherein the code in combination with the computing system is capable of performing a feedback method, said method comprising:

identifying, by said computing system, a first user, wherein said memory unit comprises a first plurality of profiles and a biomedical feedback software application, and wherein said first plurality of profiles comprises first previously received data associated with various biomedical characteristics of said first user;

enabling, by said computing system, said biomedical feedback software application for said first user;

retrieving, by said computing system from said memory unit, a first profile of said first plurality of profiles, said first profile associated with said first user and a first group of current biomedical characteristics of said first user;

monitoring, by said biomedical feedback software application, said first group of current biomedical characteristics;

analyzing, by said biomedical feedback software application, said first group of biomedical characteristics with respect to said first profile of said first plurality of profiles;

generating in response to said analyzing said first group of biomedical characteristics with respect to said first profile of said first plurality of profiles, by said biomedical feedback software application, a first analysis report comprising results of said analyzing said first group of biomedical characteristics with respect to said first profile of said first plurality of profiles; and presenting, by said computing system to said first user, said first analysis report monitoring, by said computing system, a response to said first analysis report from said first user.

The present invention advantageously provides a simple method and associated system capable monitoring user characteristics for a user and providing recommendations with respect to the user.

DETAILED DESCRIPTION OF THE INVENTION

Figure 1:
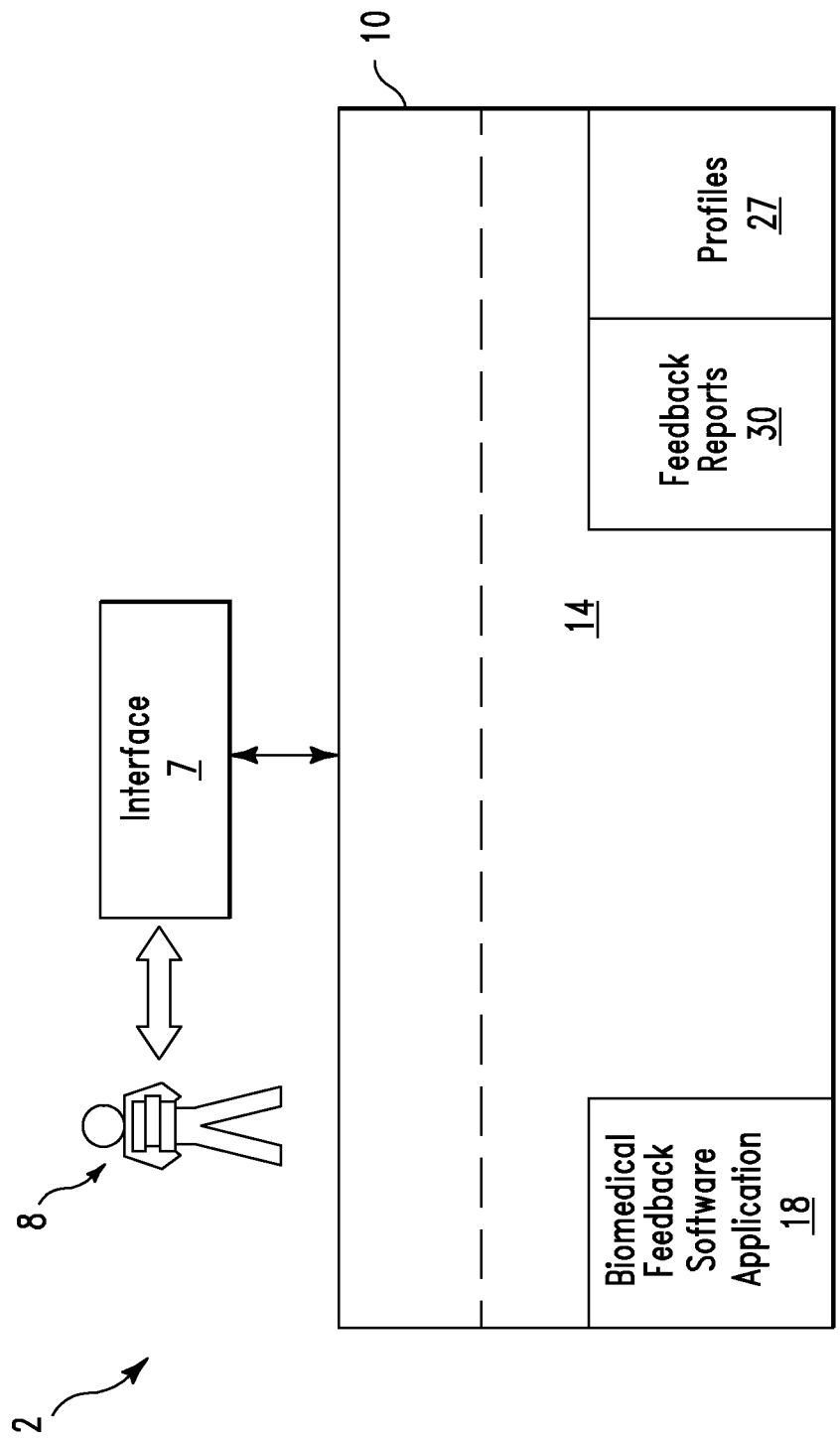
FIG. 1 illustrates a feedback system for monitoring biomedical characteristics for a user and providing feedback associated with the biomedical characteristics, in accordance with embodiments of the present invention.

FIG. 1 illustrates a feedback system 2 for monitoring biomedical characteristics for a user 8 and providing feedback associated with the biomedical characteristics, in accordance with embodiments of the present invention. Biomedical characteristics may include, inter alia, body temperature, heart rate, breathing rate, etc. The feedback (e.g., a feedback report) may comprise suggestions or recommendations for user 8 in order to optimize their biomedical characteristics.

As people become increasingly health conscious, they require feedback associated with optimizing food intake and exercise. System 2 is used to monitor user 8 movement and biomedical signals such as, inter alia, body temperature, heart rate, breathing rate, etc. Various users may be profiled in terms of movement and biomedical characteristics. The resulting profiles 27 are used to determine cardiovascular or other measures of fitness, as well as expenditures of calories. Input devices or an interface 7 (e.g., a keyboard, biomedical sensors or monitors, etc) may be integrated to allow user 8 to declare types and amounts of food and beverage consumed. These characteristics are transmitted to computing system 10. Computing system 10 performs a profile analysis and generates recommendations for increasing efficiency of motion in order to improve fitness. During analysis, a current profile may be compared to previous profiles (i.e., profiles belong to user 8 or additional users) and recommendations are generated based on the comparison. Additionally, warning signals could be generated and transmitted to a local emergency facility if the biomedical characteristics exceed a critical threshold (e.g., a heat rate exceeds a threshold, thereby indicating a possible impending cardiac arrest).

The following series of description illustrates an example for using system 2 for monitoring biomedical characteristics for user 8 and providing feedback:

Upon starting a day, an identity for user 8 is established based on a key or RFID device that user 8 is wearing (e.g., a wristwatch, an embedded sensor in a wearable device, etc.). As user 8 moves and interacts throughout the day, biomedical information is gathered (i.e., via interface 7) and stored in computing system 10. Interface 7 may comprise a any type of biomedical sensor capable of monitoring and retrieving biomedical information include, a pulse rate, a heart rate, a body temperature, etc. Examples of biomedical sensors may include, inter alia, a heart rate monitor, a blood pressure monitor, a thermometer, a pulse rate monitor, etc. The aforementioned biomedical information is retrieved and processed by computing system 10 and feedback information is generated. The feedback information may include, inter alia, types of motion or the lack thereof, increased weight as user 8 eats or drinks, monitored stress based on an increase heart rate, pulse, etc. During the day, calculations are executed based on motion and changes in biomedical signals associated with user 8. The calculations are used to recommend when and where user 8 should rest, eat, relax, etc. Additional profiling may be inputted resulting in a signal for user 8 that indicates that it is time to get up, stretch, exercise, etc. When desirable changes in various vital signs are achieved, user 8 may be signaled to stop exercising, moving, etc. System 2 may be used over a preset exercise path or types of food that should be eaten so that user 8 may gauge personal lifestyle versus a hypothetical optimum in terms of various factors. Recommendations may be made on how the user's 8 profile could be improved and how the current profile compares to past profile(s) for user 8 as well as other user profiles.

Threshold limits may be placed on vital sign readings that would cause emergency signals to be generated if the threshold limits are exceeded. The emergency signals could be used by emergency teams to respond to a victim undergoing a heart attack, stroke, etc.

System 2 of FIG. 1 comprises computing system 10 and user interface 7 (e.g., comprising a heart rate monitor, a blood pressure monitor, a thermometer, a pulse rate monitor, etc) connected to computing system 10. Computing system 10 may comprise any type of computing system including, inter alia, a personal computer (PC), a server computer, a database computer, an embedded computer, etc. Computing system 10 comprises a memory apparatus 14. Memory apparatus 14 comprises biomedical feedback software application 18, profiles 27, and feedback reports 30. Although FIG. 1 illustrates memory apparatus 14 located internal to computing system 10, note that memory apparatus 10 may optionally be located external to computing system 10 (e.g., in a remote location) and connected to computing system 10 through a communication link (e.g., a network, the Internet, etc). Interface 7 comprises all devices related to interfacing user 8 to computing system 10. Interface 7 comprises all sensors used for monitoring biomedical characteristics for user 8 as well as a monitor for presenting the feedback reports 30 to user 8.

Biomedical feedback software application 18 controls all functions related to:
1. Generating profiles 27.
2. Analyzing biomedical characteristics.
3. Generating feedback reports 30.

The following description illustrates a biomedical characteristic feedback report generation process. At initialization, biomedical feedback software application 18 displays existing profiles (via interface 7) for user 8. Additionally, an option to create a new profile may be displayed for user 8.

If an existing profile is selected, user 8 may indicate which profile will be activated. If a new profile will be created (or an existing profile modified and saved with a new name), user 8 is prompted for items such as the following to be specified:
1. Username
2. Type of user (e.g., advanced, intermediate, beginner, etc)
3. Suggestion prompting: On/Off
4. Heart Rate Monitoring (e.g., systolic, diastolic, pulse, etc): On/Off
5. EKG: On/Off
6. Body temperature: On/Off
7. Distance monitor: On/Off
8. Logging: On/Off
9. Calories consumed: On/Off
10. Heart rate pulse speed: set/not set
11. Set time: On/Off
12. Fluid Intake monitoring
13. Fluids lost via sweat Items such as the following performance results will be calculated:
1. Heart rate—sedentary
2. Calorie consumption per unit time
3. Body mass index
4. Fluids consumed/sweated—dehydration monitoring Additionally, a single session profile may be generated. The single session profile will not be saved as part of the profile library.

If an existing profile is used, user 8 may be prompted as to whether existing data should be obtained for this profile and merged with new data obtained.

Table 1 illustrates an example of a list of default profiles.

TABLE 1

| Profile Name | Program |
| --- | --- |
| Short Run | Monitor |
| Marathon | Monitor and suggest |
| 30 Minute Walk | Suggest |
| Equivalent to 30 Minute Walk | Monitor and Report |
| Monitor Only | Monitor |

Regardless of whether a new profile is generated or an existing profile is used, biomedical feedback software application 18 periodically samples various vital signs of user 8 (e.g., once per minute). If results of the vital sign sampling exceeds predefined thresholds, specific indicators involved may be transmitted back to user 8 (e.g., via: voice, display, audible sounds unique to a particular indicator). For example, pulse and fluid indicators may comprise a more noticeable sound than calories consumed.

During a sampling session, suggestions may be transmitted back to the user 8 (e.g., increase speed to consume more calories, take in more water, etc. Additionally, any of the indicators may be read out or stated verbally at a predetermined time (e.g., every 5 minutes) or upon user 8 command.

When a sampling session is terminated, the results may be tabulated, compared to existing profile results, or submitted for more exhaustive analysis depending on the user's 8 gender, age, weight, and other medical conditions.

The following description illustrates an example of implementation for monitoring biomedical characteristics for a user and providing feedback associated with the biomedical characteristics, in accordance with embodiments of the present invention.

Janice, (i.e., a user) has a wrist watch comprising interface 7. The watch senses her biomedical profile and activates a welcome with a default profile enabled (e.g., Monitor only). If the watch is not able to identify Janice, she is prompted to provide an identity and select a saved profile or create a new one. Janice confirms her profile and is prompted to specify whether previous statistics and history should be loaded for processing during her present cycle of activity (note that this may become a profile option over time). Since she is starting a new job, Janice additionally requests that a profiling analysis be turned on for benchmarking purposes. Janice confirms her identity and begins going about her usual routine (e.g., walk to a mass transit location, catch a bus, walk to her new office, and work). Computing system 10 monitors her activity (e.g., running to catch the bus, climbing stairs, walking in her office, etc) and computes statistics that predict calorie output. Periodically, computing system 10 reports profile status relative to her default profile, progress relative to goals or suggested activity relative to age, weight, etc.

Janice does not eat breakfast but does go to lunch at a regular time. Computing system 10 has her meal information stored in its profile and prompts Janice for information related to calorie intake computations. Visual selection screens are provided for Janis to select foods and amounts. Standard computations are used to estimate calories consumed. Computing system 10 estimates how many calories Janice has used vs. how many calories Janice has consumed.

Janice returns to work, completes the rest of the work day, and leaves at her usual time. She notices that computing system 10 predicts that she is under her usual level of biomedical activity for the day (e.g., number of steps taken) and also under her usual calorie expenditure. Computing system 10 recommends a brisk walk.

As a result of the recommendation, Janice decides to walk home. Upon arrival home, she requests that computing system 10 provides a biomedical update. Computing system 10 computes results and provides satisfactory results in terms of effort and calorie expenditure along with a "well done" message.

Janice confirms that the day is over and to profile and save these results. Computing system 10 confirms the update and continues to monitor Janice's activity and consumption through the remainder of the day. When Janice takes the watch off, computing system 10 provides a final report and saves the results.

Figure 2:
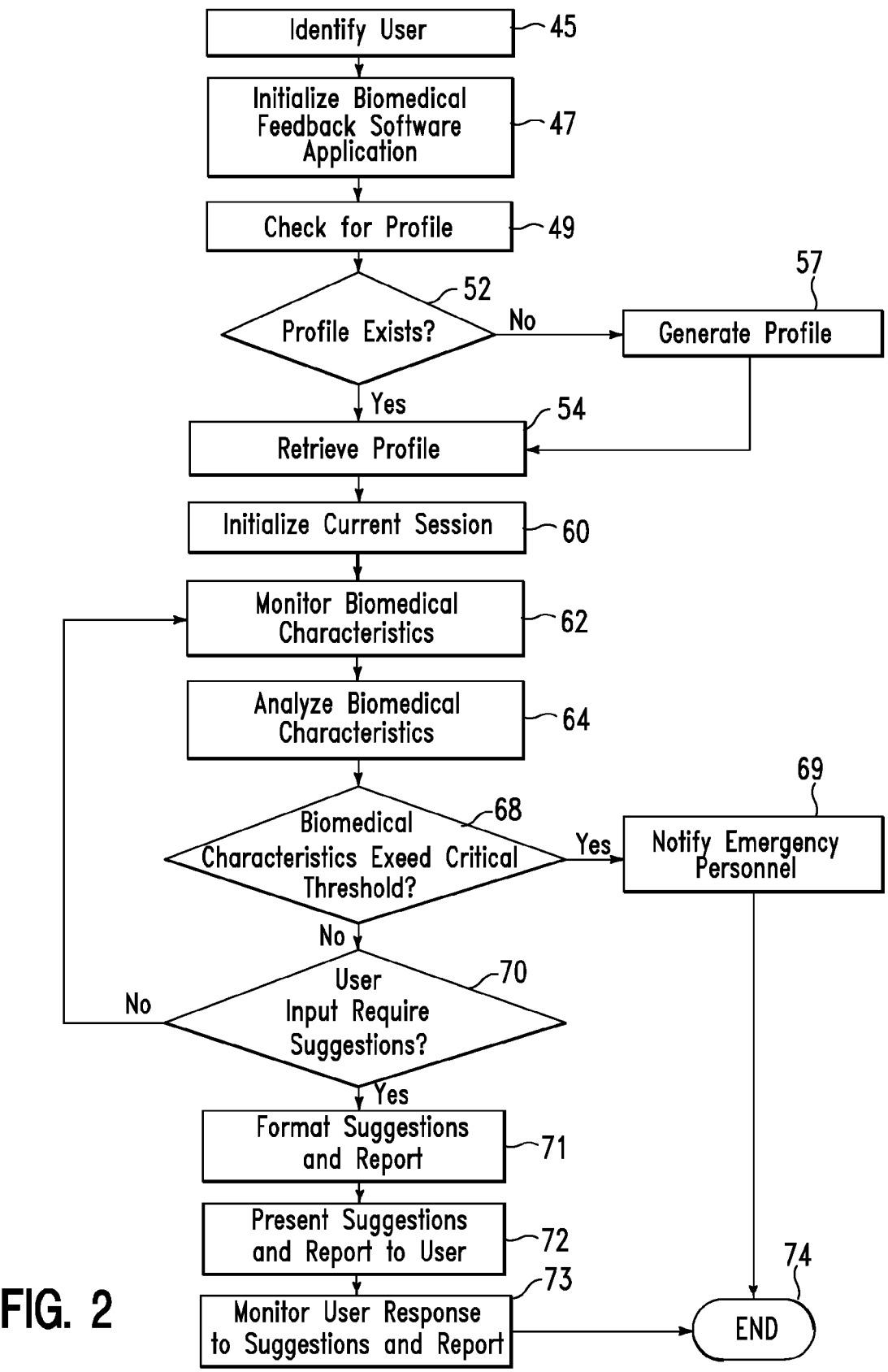
FIG. 2 illustrates a flowchart describing an example of an algorithm used by the system of FIG. 1 for monitoring biomedical characteristics for a user 8 and providing feedback associated with the biomedical characteristics, in accordance with embodiments of the present invention.

FIG. 2 illustrates a flowchart describing an example of an algorithm used by system 2 of FIG. 1 for monitoring biomedical characteristics for a user and providing feedback associated with the biomedical characteristics, in accordance with embodiments of the present invention. In step 45, a user is identified by computing system 10. In step 47, computing system 10 initializes biomedical feedback software application 18. In step 49, biomedical feedback software application 18 (in response to user request) checks memory system for profiles associated with the user. In step 52, it is determined if a requested profile is available.

If in step 52, it is determined that the requested profile is not available then in step 57 a profile generation process is performed as described with reference to FIG. 3, supra and step 54 is executed as described, supra. The profile may be stored in memory system 14.

If in step 52, it is determined that the requested profile is available then in step 54 the requested profile is retrieved from memory system 14. In step 60, a current feedback session is initialized for the user. In step 62, biomedical feedback software application 18 monitors biomedical characteristics for the user. In step 64, biomedical characteristics for the user are analyzed. The biomedical characteristics for the user are analyzed with respect to the user profile retrieved in step 54, a user profile for another user, past user input, etc.

In step 68, it is determined if the biomedical characteristics analyzed in step 64 have exceeded a critical threshold.

If in step 68, it is determined that the biomedical characteristics analyzed in step 64 have exceeded a critical threshold then in step 69 emergency personnel are notified and the process is terminated in step 74.

If in step 68, it is determined that the biomedical characteristics analyzed in step 64 have not exceeded a critical threshold then in step 70, it is determined if the biomedical characteristics analyzed in step 64 requires suggestions for optimizing various user activities (e.g., food intake, exercise, etc).

If in step 70, it is determined that the biomedical characteristics analyzed in step 64 does not require suggestions for optimizing various user activities then step 62 is repeated.

If in step 70, it is determined that the biomedical characteristics analyzed in step 64 does not require suggestions for optimizing various user activities then in step 71 suggestions are formatted and a feedback report is generated. In step 72, the feedback report is presented to the user. In step 73, feedback software application monitors user response to the suggestions and the process terminates in step 74.

Figure 3:
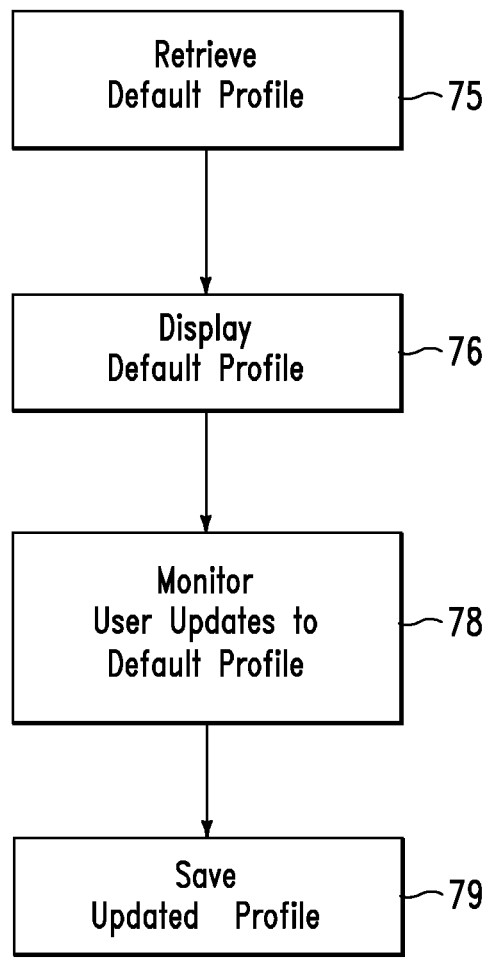
FIG. 3 illustrates a flowchart illustrating an algorithm for generating a profile, in accordance with embodiments of the present invention.

FIG. 3 illustrates a flowchart detailing step 57 of FIG. 2 for generating a profile, in accordance with embodiments of the present invention. In step 75, a default (i.e., generic) profile is retrieved. The generic profile may comprise a profile template. In step 76, the default (i.e., generic) profile is presented to the user. In step 78, the user updates the profile and biomedical feedback software application 18 monitors the updates to the profile. In step 79, the profile is named and saved.

Figure 4:
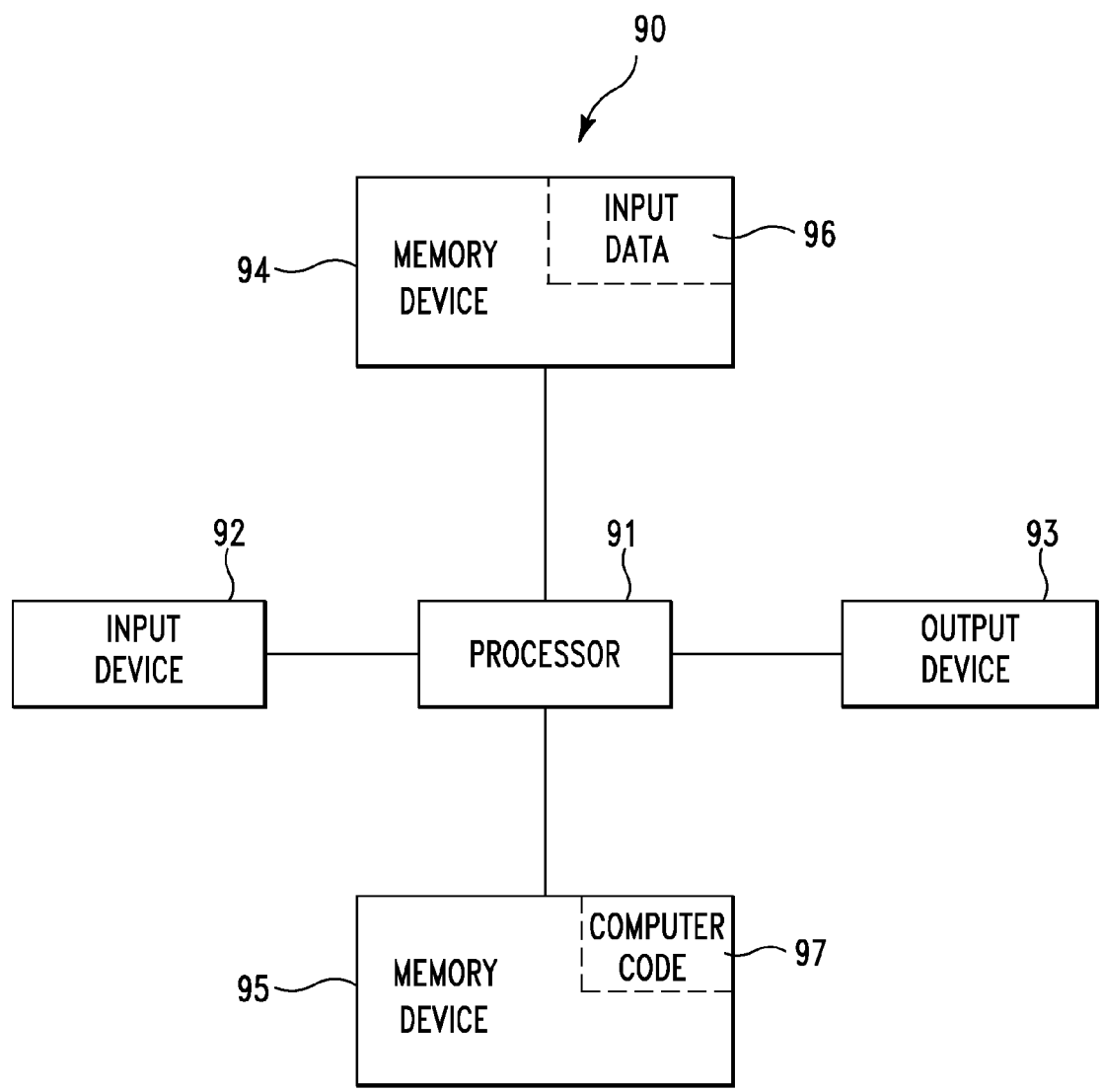
FIG. 4 illustrates a computer apparatus used for monitoring biomedical characteristics for a user and providing feedback associated with the biomedical characteristics, in accordance with embodiments of the present invention.

FIG. 4 illustrates a computer apparatus 90 (e.g., computing system 10 of FIG. 1) used for monitoring biomedical characteristics for a user 8 and providing feedback associated with the biomedical characteristics, in accordance with embodiments of the present invention. The computer system 90 comprises a processor 91, an input device 92 coupled to the processor 91, an output device 93 coupled to the processor 91, and memory devices 94 and 95 each coupled to the processor 91. The input device 92 may be, inter alia, a keyboard, a mouse, etc. The output device 93 may be, inter alia, a printer, a plotter, a computer screen, a magnetic tape, a removable hard disk, a floppy disk, etc. The memory devices 94 and 95 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 95 includes a computer code 97. The computer code 97 includes algorithms (e.g., the algorithms of FIGS. 2-3) for monitoring biomedical characteristics for a user and providing feedback associated with the biomedical characteristics. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices not shown in FIG. 4) may comprise the algorithms of FIGS. 2-3 and may be used as a computer usable medium (or a computer readable medium or a program storage device) having a computer readable program code embodied therein and/or having other data stored therein, wherein the computer readable program code comprises the computer code 97. Generally, a computer program product (or, alternatively, an article of manufacture) of the computer system 90 may comprise said computer usable medium (or said program storage device).

Still yet, any of the components of the present invention could be created, integrated, hosted, maintained, deployed, managed, serviced, etc. by a service provider who offers to monitor biomedical characteristics for a user and provide feedback associated with the biomedical characteristics. Thus the present invention discloses a process for deploying, creating, integrating, hosting, maintaining, and/or integrating computing infrastructure, comprising integrating computer-readable code into the computer system 90, wherein the code in combination with the computer system 90 is capable of performing a method for monitoring biomedical characteristics for a user 8 and providing feedback associated with the biomedical characteristics. In another embodiment, the invention provides a business method that performs the process steps of the invention on a subscription, advertising, and/or fee basis. That is, a service provider, such as a Solution Integrator, could offer to monitor biomedical characteristics for a user and provide feedback associated with the biomedical characteristics. In this case, the service provider can create, maintain, support, etc. a computer infrastructure that performs the process steps of the invention for one or more customers. In return, the service provider can receive payment from the customer(s) under a subscription and/or fee agreement and/or the service provider can receive payment from the sale of advertising content to one or more third parties.

While FIG. 4 shows the computer system 90 as a particular configuration of hardware and software, any configuration of hardware and software, as would be known to a person of ordinary skill in the art, may be utilized for the purposes stated supra in conjunction with the particular computer system 90 of FIG. 4. For example, the memory devices 94 and 95 may be portions of a single memory device rather than separate memory devices.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:
1. A feedback method comprising:
identifying, by a computing system, a first user, wherein said computing system comprises a computer processor and a memory system, wherein said memory system comprises a first plurality of profiles and a biomedical feedback software application, and wherein said first plurality of profiles comprises first previously received data associated with various biomedical characteristics of said first user;

enabling, by said computing system, said biomedical feedback software application for said first user;
retrieving, by said computing system from said memory system, a first profile of said first plurality of profiles, said first profile associated with said first user and a first group of current biomedical characteristics of said first user, wherein said first group of current biomedical characteristics comprises current vital sign readings from said first user;
monitoring, by said biomedical feedback software application, said first group of current biomedical characteristics;
analyzing, by said computer processor executing said biomedical feedback software application, said first group of biomedical characteristics with respect to said first profile of said first plurality of profiles, wherein analyzing said first group of biomedical characteristics with respect to said first profile comprises:
calculating a heart rate for said first user;
calculating a calorie consumption per unit time for said first user;
calculating a body mass index for said first user;
calculating a dehydration level for said first user; and
calculating a number of steps taken by said first user;
generating in response to said analyzing said first group of biomedical characteristics with respect to said first profile of said first plurality of profiles, by said biomedical feedback software application, a first analysis report comprising results of said analyzing said first group of biomedical characteristics with respect to said first profile of said first plurality of profiles, said first analysis report comprising said heart rate, said calorie consumption per unit time, said body mass index, said dehydration level, and said number of steps taken;
presenting, by said computing system to said first user, said first analysis report;
receiving, by said computing system, threshold levels for any vital sign readings obtained from said first user;
analyzing, by said biomedical feedback software application, said current vital sign readings from said first user with respect to said threshold levels;
determining, by said biomedical feedback software application, that a group of vital sign readings of said current vital sign readings exceed associated threshold levels of said threshold levels;
presenting, by said computing system to said first user, audible indicators indicating audible sounds associated with said group of vital sign readings exceeding said associated threshold levels, wherein each audible indicator of said audible indicators is associated with a different vital sign reading of said group of vital sign readings exceeding an associated threshold level of said associated threshold levels, and wherein each audible sound of said audible sounds comprises a different audible sound comprising a different audible level depending on an association with vital sign readings of said group of vital sign readings;
monitoring, by said computing system, a response to said first analysis report from said first user;
generating, by said computing system based on results of said analyzing said first group of biomedical characteristics, an updated profile from said first profile of said first plurality of profiles;
enabling, by said first user, a motion monitoring routine for said biomedical feedback software application;
detecting in response to said enabling said motion monitoring routine, by said biomedical feedback software application at specified intervals during a specified time period, different movement types associated with movements of said first user;
periodically monitoring in response to said different movement types, by said biomedical feedback software application at said specified intervals during said specified time period, groups of specified levels for said first group of current biomedical characteristics;
analyzing, by said biomedical feedback software application, said groups of specified levels for said first group of current biomedical characteristics with respect to said updated profile;
analyzing, by said biomedical feedback software application, said groups of specified levels with respect to a gender, age, and weight of said first user;
generating, by said biomedical feedback software application in response to said analyzing said groups of specified levels with respect to said updated profile and said analyzing said groups of specified levels with respect to said gender, said age, and said weight of said first user, caloric recommendations for calories to be consumed by said first user;
generating, by said biomedical feedback software application in response to said analyzing said groups of specified levels, motion recommendations for specified motions to be performed by said first user, wherein said specified motions include a brisk walk;
presenting, by said computing system to said first user, said caloric recommendations and said motion recommendations;
periodically monitoring in response to said presenting said caloric recommendations and said motion recommendations, by said biomedical feedback software application, additional groups of specified levels for said first group of current biomedical characteristics;
analyzing, by said biomedical feedback software application, said additional groups of specified levels for said first group of current biomedical characteristics with respect to said groups of specified levels; and
determining, by said biomedical feedback software application, if said user has performed activities associated with said caloric recommendations and said motion recommendations.

2. The method of claim 1, further comprising:
disabling, by said computing system, said biomedical feedback software application for said first user;
identifying, by said computing system, a second user, wherein said memory system comprises a second plurality of profiles, and wherein each profile of said second plurality of profiles comprises second previously received data associated with various biomedical characteristics of said second user;
enabling, by said computing system, said biomedical feedback software application for said second user;
retrieving, by said computing system from said memory system, a first profile of said second plurality of profiles, said first profile of said second plurality of profiles associated with said second user and a second group of current biomedical characteristics of said second user;
monitoring, by said feedback software application, said second group of current biomedical characteristics of said second user;
analyzing, by said biomedical feedback software application, said second group of current biomedical characteristics of said second user with respect to said first profile of said second plurality of profiles;

generating in response to said analyzing said second group of current biomedical characteristics of said second user with respect to said first profile of said second plurality of profiles, by said biomedical feedback software application, a second analysis report comprising results of said analyzing said second group of current biomedical characteristics of said second user with respect to said first profile of said second plurality of profiles; and presenting, by said computing system to said second user, said second analysis report monitoring, by said computing system, a response to said second analysis report from said second user.

3. The method of claim 2, further comprising:

analyzing, by said biomedical feedback software application, said second group of current biomedical characteristics of said second user with respect to said first group of current biomedical characteristics of said first user;

generating in response to said analyzing said second group of current biomedical characteristics of said second user with respect to said first group of current biomedical characteristics of said first user, by said feedback software application, a third analysis report comprising results of said analyzing said second group of current biomedical characteristics of said second user with respect to said first group of current biomedical characteristics of said first user;

presenting, by said computing system to said second user, said third analysis report; and monitoring, by said computing system, a response to said third analysis report from said second user.

4. The method of claim 1, further comprising:

generating, by said computing system, a warning signal; and transmitting, by said computing system, said warning signal to a medical emergency dispatcher.

5. The method of claim 1, wherein said first analysis report comprises suggestions for said first user, said suggestions comprising recommendations for: exercise start/stop times, eating times, and food types for consumption.

6. A computing system comprising a processor coupled to a computer-readable memory unit, said memory unit comprising a first plurality of profiles, a biomedical feedback software application, and instructions that when executed by the processor implement a feedback method, wherein said first plurality of profiles comprises first previously received data associated with various biomedical characteristics of a first user, said method comprising:

identifying, by said computing system, said first user;

enabling, by said computing system, said biomedical feedback software application for said first user;

retrieving, by said computing system from said computer-readable memory unit, a first profile of said first plurality of profiles, said first profile associated with said first user and a first group of current biomedical characteristics of said first user, wherein said first group of current biomedical characteristics comprises current vital sign readings from said first user;

monitoring, by said biomedical feedback software application, said first group of current biomedical characteristics;

analyzing, by said biomedical feedback software application, said first group of biomedical characteristics with respect to said first profile of said first plurality of profiles, wherein analyzing said first group of biomedical characteristics with respect to said first profile comprises:

calculating a heart rate for said first user;
calculating a calorie consumption per unit time for said first user
calculating a body mass index for said first user;
calculating a dehydration level for said first user; and
calculating a number of steps taken by said first user;

generating in response to said analyzing said first group of biomedical characteristics with respect to said first profile of said first plurality of profiles, by said biomedical feedback software application, a first analysis report comprising results of said analyzing said first group of biomedical characteristics with respect to said first profile of said first plurality of profiles, said first analysis report comprising said heart rate, said calorie consumption per unit time, said body mass index, said dehydration level, and said number of steps taken;

presenting, by said computing system to said first user, said first analysis report;

receiving, by said computing system, threshold levels for any vital sign readings obtained from said first user;

analyzing, by said biomedical feedback software application, said current vital sign readings from said first user with respect to said threshold levels;

determining, by said biomedical feedback software application, that a group of vital sign readings of said current vital sign readings exceed associated threshold levels of said threshold levels;

presenting, by said computing system to said first user, audible indicators indicating audible sounds associated with said group of vital sign readings exceeding said associated threshold levels, wherein each audible indicator of said audible indicators is associated with a different vital sign reading of said group of vital sign readings exceeding an associated threshold level of said associated threshold levels, and wherein each audible sound of said audible sounds comprises a different audible sound comprising a different audible level depending on an association with vital sign readings of said group of vital sign readings;

monitoring, by said computing system, a response to said first analysis report from said first user;

generating, by said computing system based on results of said analyzing said first group of biomedical characteristics, an updated profile from said first profile of said first plurality of profiles;

enabling, by said first user, a motion monitoring routine for said biomedical feedback software application;

detecting in response to said enabling said motion monitoring routine, by said biomedical feedback software application at specified intervals during a specified time period, different movement types associated with movements of said first user;

periodically monitoring in response to said different movement types, by said biomedical feedback software application at said specified intervals during said specified time period, groups of specified levels for said first group of current biomedical characteristics;

analyzing, by said biomedical feedback software application, said groups of specified levels for said first group of current biomedical characteristics with respect to said updated profile;

analyzing, by said biomedical feedback software application, said groups of specified levels with respect to a gender, age, and weight of said first user;

generating, by said biomedical feedback software application in response to said analyzing said groups of specified levels with respect to said updated profile and said analyzing said groups of specified levels with respect to said gender, said age, and said weight of said first user, caloric recommendations for calories to be consumed by said first user;

generating, by said biomedical feedback software application in response to said analyzing said groups of specified levels, motion recommendations for specified motions to be performed by said first user, wherein said specified motions include a brisk walk;

presenting, by said computing system to said first user, said caloric recommendations and said motion recommendations;

periodically monitoring in response to said presenting said caloric recommendations and said motion recommendations, by said biomedical feedback software application, additional groups of specified levels for said first group of current biomedical characteristics;

analyzing, by said biomedical feedback software application, said additional groups of specified levels for said first group of current biomedical characteristics with respect to said groups of specified levels; and determining, by said biomedical feedback software application, if said user has performed activities associated with said caloric recommendations and said motion recommendations.

7. The computing system of claim 6, wherein said method further comprises:

disabling, by said computing system, said biomedical feedback software application for said first user;

identifying, by said computing system, a second user, wherein said computer-readable memory unit comprises a second plurality of profiles, and wherein each profile of said second plurality of profiles comprises second previously received data associated with various biomedical characteristics of said second user;

enabling, by said computing system, said biomedical feedback software application for said second user;

retrieving, by said computing system from said computer-readable memory unit, a first profile of said second plurality of profiles, said first profile of said second plurality of profiles associated with said second user and a second group of current biomedical characteristics of said second user;

monitoring, by said feedback software application, said second group of current biomedical characteristics of said second user;

analyzing, by said biomedical feedback software application, said second group of current biomedical characteristics of said second user with respect to said first profile of said second plurality of profiles;

generating in response to said analyzing said second group of current biomedical characteristics of said second user with respect to said first profile of said second plurality of profiles, by said biomedical feedback software application, a second analysis report comprising results of said analyzing said second group of current biomedical characteristics of said second user with respect to said first profile of said second plurality of profiles; and presenting, by said computing system to said second user, said second analysis report monitoring, by said computing system, a response to said second analysis report from said second user.

8. The computing system of claim 7, wherein said method further comprises:

analyzing, by said biomedical feedback software application, said second group of current biomedical characteristics of said second user with respect to said first group of current biomedical characteristics of said first user;

generating in response to said analyzing said second group of current biomedical characteristics of said second user with respect to said first group of current biomedical characteristics of said first user, by said feedback software application, a third analysis report comprising results of said analyzing said second group of current biomedical characteristics of said second user with respect to said first group of current biomedical characteristics of said first user;

presenting, by said computing system to said second user, said third analysis report; and monitoring, by said computing system, a response to said third analysis report from said second user.

9. The computing system of claim 6, wherein said analyzing said current vital sign readings from said first user with respect to said threshold levels determines that said vital sign reading exceeds said associated threshold level of said threshold levels, and wherein said method further comprises:

generating, by said computing system, a warning signal; and transmitting, by said computing system, said warning signal to a medical emergency dispatcher.

10. The computing system of claim 6, wherein said first analysis report comprises suggestions for said first user, said suggestions comprising recommendations for: exercise start/stop times, eating times, and food types for consumption.

11. A computer program product, comprising a computer readable storage device storing a computer readable program code embodied therein, said computer readable program code adapted to implement a feedback method within a computing system, said method comprising:

identifying, by said computing system, a first user, wherein said computer readable medium comprises a first plurality of profiles and a biomedical feedback software application, and wherein said first plurality of profiles comprises first previously received data associated with various biomedical characteristics of said first user;

enabling, by said computing system, said biomedical feedback software application for said first user;

retrieving, by said computing system from said computer readable medium, a first profile of said first plurality of profiles, said first profile associated with said first user and a first group of current biomedical characteristics of said first user, wherein said first group of current biomedical characteristics comprises current vital sign readings from said first user;

monitoring, by said biomedical feedback software application, said first group of current biomedical characteristics;

analyzing, by said biomedical feedback software application, said first group of biomedical characteristics with respect to said first profile of said first plurality of profiles, wherein analyzing said first group of biomedical characteristics with respect to said first profile comprises:

calculating a heart rate for said first user;

calculating a calorie consumption per unit time for said first user calculating a body mass index for said first user;

calculating a dehydration level for said first user; and calculating a number of steps taken by said first user;

generating in response to said analyzing said first group of biomedical characteristics with respect to said first profile of said first plurality of profiles, by said biomedical feedback software application, a first analysis report comprising results of said analyzing said first group of biomedical characteristics with respect to said first profile of said first plurality of profiles, said first analysis report comprising said heart rate, said calorie consumption per unit time, said body mass index, said dehydration level, and said number of steps taken;

presenting, by said computing system to said first user, said first analysis report;

receiving, by said computing system, threshold levels for any vital sign readings obtained from said first user;

analyzing, by said biomedical feedback software application, said current vital sign readings from said first user with respect to said threshold levels;

determining, by said biomedical feedback software application, that a group of vital sign readings of said current vital sign readings exceed associated threshold levels of said threshold levels;

presenting, by said computing system to said first user, audible indicators indicating audible sounds associated with said group of vital sign readings exceeding said associated threshold levels, wherein each audible indicator of said audible indicators is associated with a different vital sign reading of said group of vital sign readings exceeding an associated threshold level of said associated threshold levels, and wherein each audible sound of said audible sounds comprises a different audible sound comprising a different audible level depending on an association with vital sign readings of said group of vital sign readings;

monitoring, by said computing system, a response to said first analysis report from said first user;

generating, by said computing system based on results of said analyzing said first group of biomedical characteristics, an updated profile from said first profile of said first plurality of profiles;

enabling, by said first user, a motion monitoring routine for said biomedical feedback software application;

detecting in response to said enabling said motion monitoring routine, by said biomedical feedback software application at specified intervals during a specified time period, different movement types associated with movements of said first user;

periodically monitoring in response to said different movement types, by said biomedical feedback software application at said specified intervals during said specified time period, groups of specified levels for said first group of current biomedical characteristics;

analyzing, by said biomedical feedback software application, said groups of specified levels for said first group of current biomedical characteristics with respect to said updated profile;

analyzing, by said biomedical feedback software application, said groups of specified levels with respect to a gender, age, and weight of said first user;

generating, by said biomedical feedback software application in response to said analyzing said groups of specified levels with respect to said updated profile and said analyzing said groups of specified levels with respect to said gender, said age, and said weight of said first user, caloric recommendations for calories to be consumed by said first user;

generating, by said biomedical feedback software application in response to said analyzing said groups of specified levels, motion recommendations for specified motions to be performed by said first user, wherein said specified motions include a brisk walk;

presenting, by said computing system to said first user, said caloric recommendations and said motion recommendations;

periodically monitoring in response to said presenting said caloric recommendations and said motion recommendations, by said biomedical feedback software application, additional groups of specified levels for said first group of current biomedical characteristics;

analyzing, by said biomedical feedback software application, said additional groups of specified levels for said first group of current biomedical characteristics with respect to said groups of specified levels; and determining, by said biomedical feedback software application, if said user has performed activities associated with said caloric recommendations and said motion recommendations.

12. The computer program product of claim 11, wherein said method further comprises:

disabling, by said computing system, said biomedical feedback software application for said first user;

identifying, by said computing system, a second user, wherein said computer readable medium comprises a second plurality of profiles, and wherein each profile of said second plurality of profiles comprises second previously received data associated with various biomedical characteristics of said second user;

enabling, by said computing system, said biomedical feedback software application for said second user;

retrieving, by said computing system from said computer readable medium, a first profile of said second plurality of profiles, said first profile of said second plurality of profiles associated with said second user and a second group of current biomedical characteristics of said second user;

monitoring, by said feedback software application, said second group of current biomedical characteristics of said second user;

analyzing, by said biomedical feedback software application, said second group of current biomedical characteristics of said second user with respect to said first profile of said second plurality of profiles;

generating in response to said analyzing said second group of current biomedical characteristics of said second user with respect to said first profile of said second plurality of profiles, by said biomedical feedback software application, a second analysis report comprising results of said analyzing said second group of current biomedical characteristics of said second user with respect to said first profile of said second plurality of profiles; and presenting, by said computing system to said second user, said second analysis report monitoring, by said computing system, a response to said second analysis report from said second user.

13. The computer program product of claim 12, wherein said method further comprises:

analyzing, by said biomedical feedback software application, said second group of current biomedical characteristics of said second user with respect to said first group of current biomedical characteristics of said first user;

generating in response to said analyzing said second group of current biomedical characteristics of said second user with respect to said first group of current biomedical characteristics of said first user, by said feedback software application, a third analysis report comprising results of said analyzing said second group of current biomedical characteristics of said second user with respect to said first group of current biomedical characteristics of said first user;

presenting, by said computing system to said second user, said third analysis report; and monitoring, by said computing system, a response to said third analysis report from said second user.

14. The computer program product of claim 11, wherein said method further comprises:

generating, by said computing system, a warning signal; and transmitting, by said computing system, said warning signal to a medical emergency dispatcher.

15. The computer program product of claim 11, wherein said first analysis report comprises suggestions for said first user, said suggestions comprising recommendations for: exercise start/stop times, eating times, and food types for consumption.

16. A process for supporting computer infrastructure, said process comprising providing at least one support service for at least one of creating, integrating, hosting, maintaining, and deploying computer-readable code in a computing system comprising a computer processor and a memory unit, wherein the code is executed by the computer processor as part of the process to perform a feedback method, said method comprising:

identifying, by said computing system, a first user, wherein said memory unit comprises a first plurality of profiles and a biomedical feedback software application, and wherein said first plurality of profiles comprises first previously received data associated with various biomedical characteristics of said first user;

enabling, by said computing system, said biomedical feedback software application for said first user;

retrieving, by said computing system from said memory unit, a first profile of said first plurality of profiles, said first profile associated with said first user and a first group of current biomedical characteristics of said first user, wherein said first group of current biomedical characteristics comprises current vital sign readings from said first user;

monitoring, by said biomedical feedback software application, said first group of current biomedical characteristics;

analyzing, by said computer processor executing said biomedical feedback software application, said first group of biomedical characteristics with respect to said first profile of said first plurality of profiles, wherein analyzing said first group of biomedical characteristics with respect to said first profile comprises:

calculating a heart rate for said first user;

calculating a calorie consumption per unit time for said first user;

calculating a body mass index for said first user;

calculating a dehydration level for said first user; and calculating a number of steps taken by said first user;

generating in response to said analyzing said first group of biomedical characteristics with respect to said first profile of said first plurality of profiles, by said biomedical feedback software application, a first analysis report comprising results of said analyzing said first group of biomedical characteristics with respect to said first profile of said first plurality of profiles, said first analysis report comprising said heart rate, said calorie consumption per unit time, said body mass index, said dehydration level, and said number of steps taken;

presenting, by said computing system to said first user, said first analysis report;

receiving, by said computing system, threshold levels for any vital sign readings obtained from said first user;

analyzing, by said biomedical feedback software application, said current vital sign readings from said first user with respect to said threshold levels;

determining, by said biomedical feedback software application, that a group of vital sign readings of said current vital sign readings exceed associated threshold levels of said threshold levels;

presenting, by said computing system to said first user, audible indicators indicating audible sounds associated with said group of vital sign readings exceeding said associated threshold levels, wherein each audible indicator of said audible indicators is associated with a different vital sign reading of said group of vital sign readings exceeding an associated threshold level of said associated threshold levels, and wherein each audible sound of said audible sounds comprises a different audible sound comprising a different audible level depending on an association with vital sign readings of said group of vital sign readings;

monitoring, by said computing system, a response to said first analysis report from said first user;

generating, by said computing system based on results of said analyzing said first group of biomedical characteristics, an updated profile from said first profile of said first plurality of profiles;

enabling, by said first user, a motion monitoring routine for said biomedical feedback software application;

detecting in response to said enabling said motion monitoring routine, by said biomedical feedback software application at specified intervals during a specified time period, different movement types associated with movements of said first user;

periodically monitoring in response to said different movement types, by said biomedical feedback software application at said specified intervals during said specified time period, groups of specified levels for said first group of current biomedical characteristics;

analyzing, by said biomedical feedback software application, said groups of specified levels for said first group of current biomedical characteristics with respect to said updated profile;

analyzing, by said biomedical feedback software application, said groups of specified levels with respect to a gender, age, and weight of said first user;

generating, by said biomedical feedback software application in response to said analyzing said groups of specified levels with respect to said updated profile and said analyzing said groups of specified levels with respect to said gender, said age, and said weight of said first user, caloric recommendations for calories to be consumed by said first user;

generating, by said biomedical feedback software application in response to said analyzing said groups of specified levels, motion recommendations for specified motions to be performed by said first user, wherein said specified motions include a brisk walk;

presenting, by said computing system to said first user, said caloric recommendations and said motion recommendations;

periodically monitoring in response to said presenting said caloric recommendations and said motion recommendations, by said biomedical feedback software application, additional groups of specified levels for said first group of current biomedical characteristics;

analyzing, by said biomedical feedback software application, said additional groups of specified levels for said first group of current biomedical characteristics with respect to said groups of specified levels; and determining, by said biomedical feedback software application, if said user has performed activities associated with said caloric recommendations and said motion recommendations.

17. The process of claim 16, wherein said method further comprises:

disabling, by said computing system, said biomedical feedback software application for said first user;

identifying, by said computing system, a second user, wherein said memory unit comprises a second plurality of profiles, and wherein each profile of said second plurality of profiles comprises second previously received data associated with various biomedical characteristics of said second user;

enabling, by said computing system, said biomedical feedback software application for said second user;

retrieving, by said computing system from said memory unit, a first profile of said second plurality of profiles, said first profile of said second plurality of profiles associated with said second user and a second group of current biomedical characteristics of said second user;

monitoring, by said feedback software application, said second group of current biomedical characteristics of said second user;

analyzing, by said biomedical feedback software application, said second group of current biomedical characteristics of said second user with respect to said first profile of said second plurality of profiles;

generating in response to said analyzing said second group of current biomedical characteristics of said second user with respect to said first profile of said second plurality of profiles, by said biomedical feedback software application, a second analysis report comprising results of said analyzing said second group of current biomedical characteristics of said second user with respect to said first profile of said second plurality of profiles; and presenting, by said computing system to said second user, said second analysis report monitoring, by said computing system, a response to said second analysis report from said second user.

18. The process of claim 17, wherein said method further comprises:

analyzing, by said biomedical feedback software application, said second group of current biomedical characteristics of said second user with respect to said first group of current biomedical characteristics of said first user;

generating in response to said analyzing said second group of current biomedical characteristics of said second user with respect to said first group of current biomedical characteristics of said first user, by said feedback software application, a third analysis report comprising results of said analyzing said second group of current biomedical characteristics of said second user with respect to said first group of current biomedical characteristics of said first user;

presenting, by said computing system to said second user, said third analysis report; and monitoring, by said computing system, a response to said third analysis report from said second user.

19. The process of claim 16, wherein said method further comprises:

generating, by said computing system, a warning signal; and transmitting, by said computing system, said warning signal to a medical emergency dispatcher.

20. The process of claim 16, wherein said first analysis report comprises suggestions for said first user, said suggestions comprising recommendations for: exercise start/stop times, eating times, and food types for consumption.

* * * * *